(12) United States Patent
Zeldin

(10) Patent No.: US 8,925,564 B2
(45) Date of Patent: Jan. 6, 2015

(54) PORTABLE STEAM SAUNA

(75) Inventor: Adina P. Zeldin, Brooklyn, NY (US)

(73) Assignee: Steamflex Corporation, Brooklyn, NY (US)

( * ) Notice: Subject to any disclaimer, the term of this patent is extended or adjusted under 35 U.S.C. 154(b) by 177 days.

(21) Appl. No.: 13/589,811

(22) Filed: Aug. 20, 2012

(65) Prior Publication Data

US 2013/0098415 A1  Apr. 25, 2013

Related U.S. Application Data

(60) Provisional application No. 61/549,494, filed on Oct. 20, 2011.

(51) Int. Cl.
| | | |
|---|---|---|
| *E04H 15/02* | (2006.01) | |
| *A61H 33/06* | (2006.01) | |
| *E04H 15/12* | (2006.01) | |
| *E04H 15/42* | (2006.01) | |

(52) U.S. Cl.
CPC .............. *A61H 33/066* (2013.01); *E04H 15/12* (2013.01); *E04H 15/425* (2013.01); *A61H 2033/061* (2013.01); *A61H 2033/068* (2013.01); *A61H 2201/0157* (2013.01); *A61H 2201/0161* (2013.01); *A61H 2201/10* (2013.01); *A61N 2205/0659* (2013.01)
USPC ............... 135/96; 135/92; 135/137; 135/126; 4/527; 603/83

(58) Field of Classification Search
CPC ......... E04H 15/02; E04H 15/36; E04H 15/10; E04H 15/12; E04H 2015/208; E04H 2015/207; A61H 33/06; A61H 33/10; A61H 33/063; A61H 33/065; A61H 2201/50; A61H 2033/068; A61H 2201/0157

USPC ....................... 135/96, 91–92, 124–126, 128, 135/135–137, 116, 150; 4/524, 526–529, 4/534; 607/81–83, 100
See application file for complete search history.

(56) References Cited

U.S. PATENT DOCUMENTS

| | | | | |
|---|---|---|---|---|
| 3,092,843 | A * | 6/1963 | Wright | 4/527 |
| 4,753,239 | A * | 6/1988 | Vitolo | 607/95 |
| 5,425,753 | A * | 6/1995 | Wege et al. | 607/83 |
| 5,870,780 | A * | 2/1999 | Prommer | 4/527 |
| 5,913,322 | A * | 6/1999 | Gallant et al. | 135/137 |
| 6,167,898 | B1 * | 1/2001 | Larga et al. | 135/137 |
| 6,510,565 | B1 * | 1/2003 | Zwezdaryk | 4/531 |
| 7,481,234 | B1 * | 1/2009 | Gustafson et al. | 135/91 |
| 7,698,756 | B1 * | 4/2010 | Chen | 5/113 |
| 8,342,197 | B2 * | 1/2013 | Roman et al. | 135/125 |
| 2005/0177938 | A1 * | 8/2005 | Steiner | 5/121 |
| 2008/0196152 | A1 * | 8/2008 | Lozano | 4/527 |

* cited by examiner

*Primary Examiner* — Winnie Yip

(57) ABSTRACT

A portable steam sauna includes a collapsible canopy which can be deployed in a use or storage configuration, allowing for easy deployment and transportation. The collapsible canopy has two flexible poles which provide a framework to the collapsible canopy. The collapsible canopy and flexible poles can be secured to a base sheet, which itself is attached to a flat surface such as a massage table. The collapsible canopy and base sheet each have elastic perimeters which allow them to be stretched over a flat surface, similar to how a sheet is fitted to a mattress. The base sheet includes attachment points which interface with the flexible poles and help to secure the collapsible canopy in a use configuration. Steam is supplied to the canopy by means of a steam generator, steam hose, and a steam connector which is inserted through a steam opening on the collapsible canopy.

10 Claims, 12 Drawing Sheets

PORTABLE STEAM SAUNA

The current application claims a priority to the U.S. Provisional Patent application Ser. No. 61/549,494 filed on Oct. 20, 2011.

FIELD OF THE INVENTION

The present invention relates generally to an apparatus and method for steam canopies. More specifically, the present invention is an apparatus and method for a portable steam sauna used in conjunction with steam spa treatments.

BACKGROUND OF THE INVENTION

Figure 1:
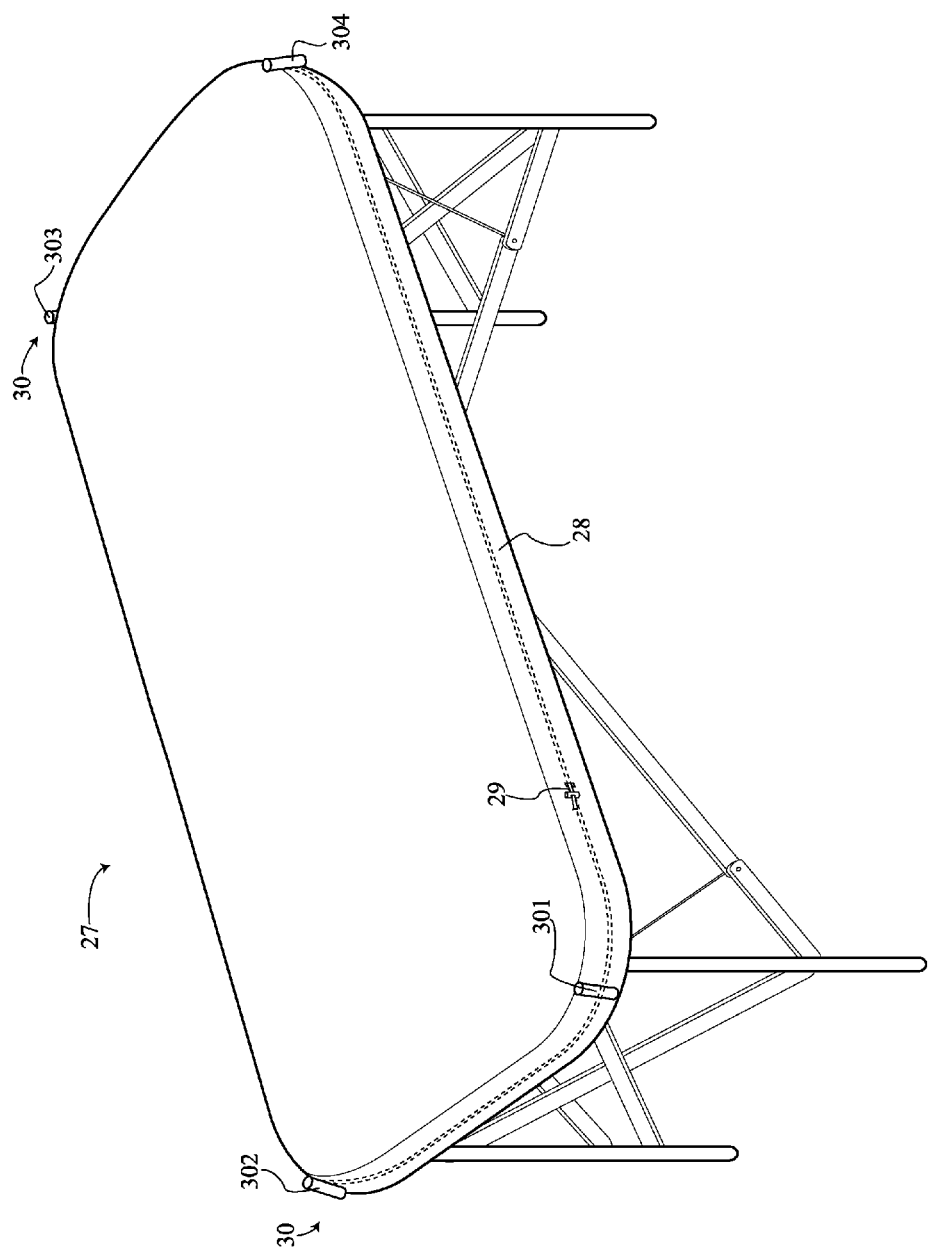
FIG. 1 is a front-right perspective view of the base sheet of the present invention.

The use of personal steam spas has become a popular method for treatment by physical and massage therapist as well as chiropractors and other professionals in the spa services and sports medicine fields. The problem with the current state of the art steam spas are that they are large, expensive units which require a great deal of space.

These large units can cause problems, especially in cities or other areas where space is of great concern. Many individuals, spas, therapists and other professionals desire to have access to a steam spa; however, the space requirement makes these units impractical as they are hard to move, not easy to store, and few even provide the capacity to be disassembled to take up less space.

A few attempts have been made to make collapsible steam canopies, such as that of U.S. Pat. No. 5,425,753 to Wege et al., hereinafter referred to as the '753 patent. However, the canopies disclosed in the '735 patent and similar steam canopies are not easily or readily collapsible. Although the '753 patent claims a collapsible canopy, it is not truly collapsible, but rather it is able to be disassembled.

In addition, much work is required to disassemble the assembled canopy disclosed in the '753 patent. For instance, in the embodiment described in the '735 patent, the poles which provide a rigid structure to the canopy must be first removed from their respective sleeves and then collapsed into smaller units. Only then is the canopy capable of being collapsed.

There are other drawbacks with existing portable sauna systems. One example is that many saunas are only usable in an upright position; they are not designed to be used by people in a supine or prone position.

There is a need in the art to provide an easily collapsible and portable steam canopy which does not require significant amounts of time or energy to collapse. Furthermore, there is a need in the art to provide a collapsible canopy that is easily stored and takes up a minimal amount of space while being usable in an upright, prone, or supine position.

It is therefore an object of the present invention to provide a collapsible steam canopy which does not require any disassembly, but instead can be folded by the force of an individual's hands for easy storage and increased portability.

DETAIL DESCRIPTIONS OF THE INVENTION

All illustrations of the drawings are for the purpose of describing selected versions of the present invention and are not intended to limit the scope of the present invention.

The present invention is a portable steam sauna which comprises a collapsible canopy 1, a first flexible pole 12, a second flexible pole 15, a steam generator 18, a steam hose 19, a steam connector 22, and a base sheet 27. The first flexible pole 12 and second flexible pole 15 are attached to the collapsible canopy 1 and provide a framework for securing the collapsible canopy 1 in a use or storage configuration. The collapsible canopy 1, the first flexible pole 12, and the second flexible pole 15 are secured to the base sheet 27 during use. The steam generator 18 supplies steam to the collapsible canopy 1 through an attached steam hose 19, which is attached to the collapsible canopy 1 by means of a steam connector 22.

Figure 3:
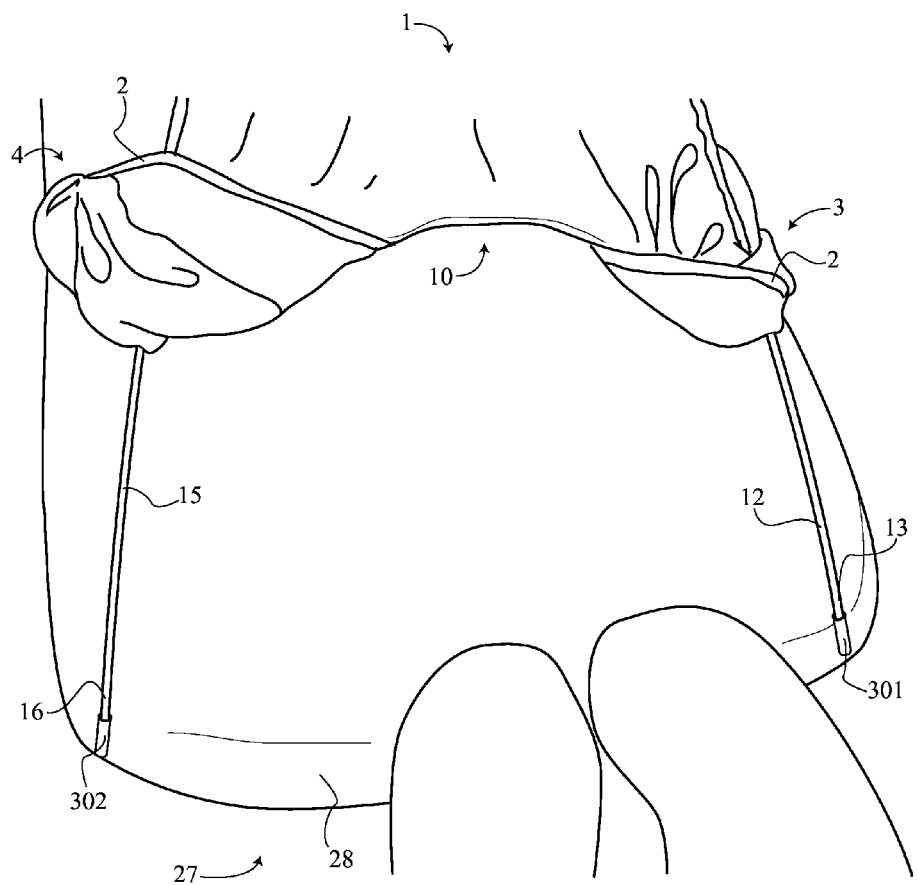
FIG. 3 is a front elevated view of the base sheet and collapsible canopy of the present invention.
Figure 4:
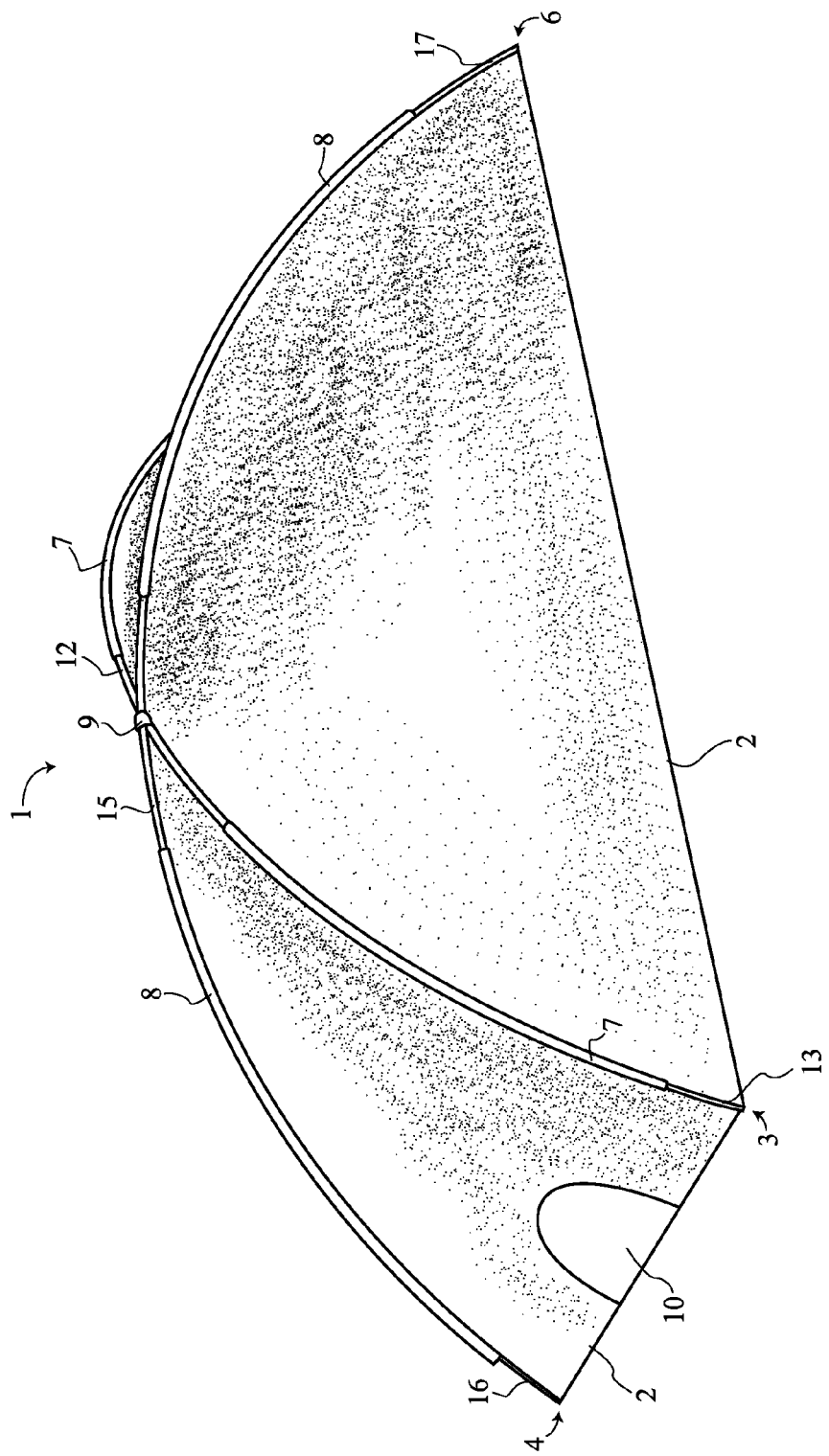
FIG. 4 is a front-right perspective view of the collapsible canopy of the present invention.
Figure 5:
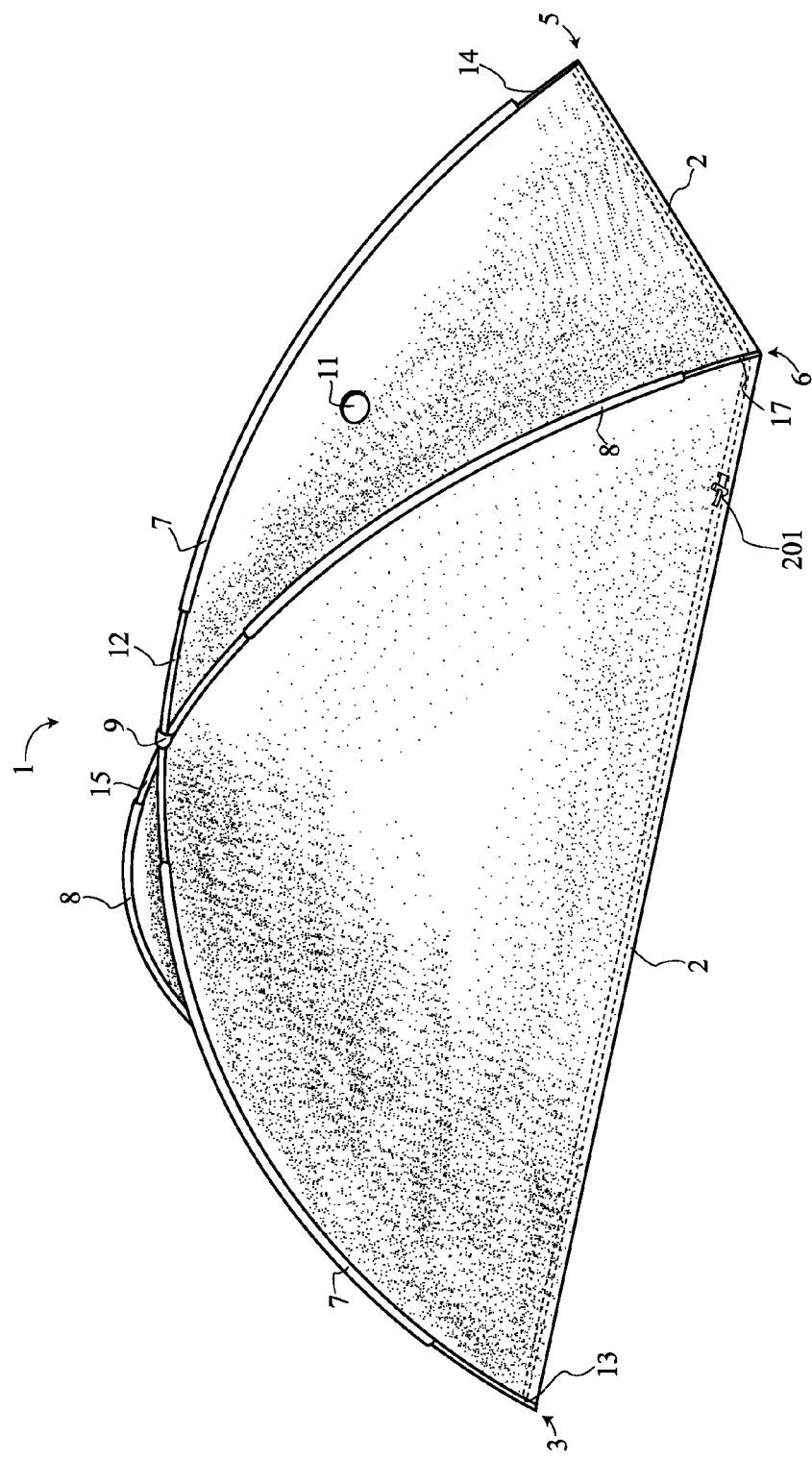
FIG. 5 is a rear-right perspective view of the collapsible canopy of the present invention.

The collapsible canopy 1, as illustrated in FIG. 3, FIG. 4, and FIG. 5, further comprises an elastic canopy perimeter 2, a first corner 3, a second corner 4, a third corner 5, a fourth corner 6, a first set of elongated sleeves 7, a second set of elongated sleeves 8, a central sleeve 9, a head opening 10, and a steam opening 11. The collapsible canopy 1 is a single surface, with a rectangular shaped bottom opening. The elastic canopy perimeter 2 is located adjacent to the bottom opening, with a first corner 3, second corner 4, third corner 5, and fourth corner 6 being located on the elastic canopy perimeter 2. The corners are consecutively positioned around the elastic canopy perimeter 2. The edge between the first corner 3 and second corner 4, as well as the edge between the third corner 5 and fourth corner 6, form short edges of the collapsible canopy 1. The edge between the first corner 3 and the fourth corner 6, as well as the edge between the second corner 4 and the third corner 5, form long edges of the collapsible canopy 1. The first set of elongated sleeves 7 and second set of elongated sleeves 8 run along the surface of the collapsible canopy 1, connecting opposite corners. The first set of elongated sleeves 7 creates a linear path from the first corner 3 to the third corner 5. The second set of elongated sleeves 8 creates a linear path from the second corner 4 to the fourth corner 6. The central sleeve 9 is located on the center of the collapsible canopy 1, equidistant from each of the corners on the elastic canopy perimeter 2. The first set of elongated sleeves 7, second set of elongated sleeves 8, and central sleeve 9 are intended to receive the flexible poles, which confer some rigidity to the collapsible canopy 1. The head opening 10 is located on a short edge of the collapsible canopy 1, seen in FIG. 4, between the first corner 3 and the second corner 4. The head opening 10 is adjacent to the elastic canopy perimeter 2 and allows a user's head to stick out of the present invention when in a use configuration. The steam opening 11 is located opposite the head opening 10, as in FIG. 5, on the short edge between the third and fourth corner 6, and is intended to receive the steam connector 22.

In the preferred embodiment the collapsible canopy 1 is made of a water-resistant nylon material. In other embodiments the collapsible canopy 1 can be made of different fabrics, or even separate materials all together. Ideally, the material used for the collapsible canopy 1 will be flexible and water-resistant, allowing the collapsible canopy 1 to be changed from a use configuration to a storage configuration as well as allowing the collapsible canopy 1 to contain the steam from the steam generator 18 without damage. The first set of elongated sleeves 7 and second set of elongated sleeves 8 each comprise two sleeves, leaving a gap in the center of the collapsible canopy 1 to place the central sleeve 9. Thus there would be a single sleeve between the center and each corner of the elastic canopy perimeter 2. In other embodiments the first set of elongated sleeves 7 and second set of elongated sleeves 8 could include a larger number of individual sleeves; the amount of individual sleeves is not particularly important, as long as each set of sleeves leaves a center gap for the central sleeve 9. The sleeves can be made of fabric or any flexible material, allowing the sleeves to flex with the poles when the collapsible canopy 1 is in a storage configuration.

The elastic canopy perimeter 2 further comprises a canopy cord 201, pictured in FIG. 5. The canopy cord 201 can be used to tighten or loosen the elastic canopy perimeter 2. The tightening and loosening of the elastic canopy perimeter 2 can be accomplished by pulling or releasing the canopy cord 201. The canopy cord 201 can be secured in a tightened or slackened state by including a cord lock or similar device as part of the canopy cord 201. The elastic nature of the elastic canopy perimeter 2 will allow it to stretch over and be fitted to the base sheet 27, similar to how bedding sheets are secured to a mattress. Tightening the canopy cord 201 then helps to further secure the elastic canopy perimeter 2 to the base sheet 27.

Figure 2:
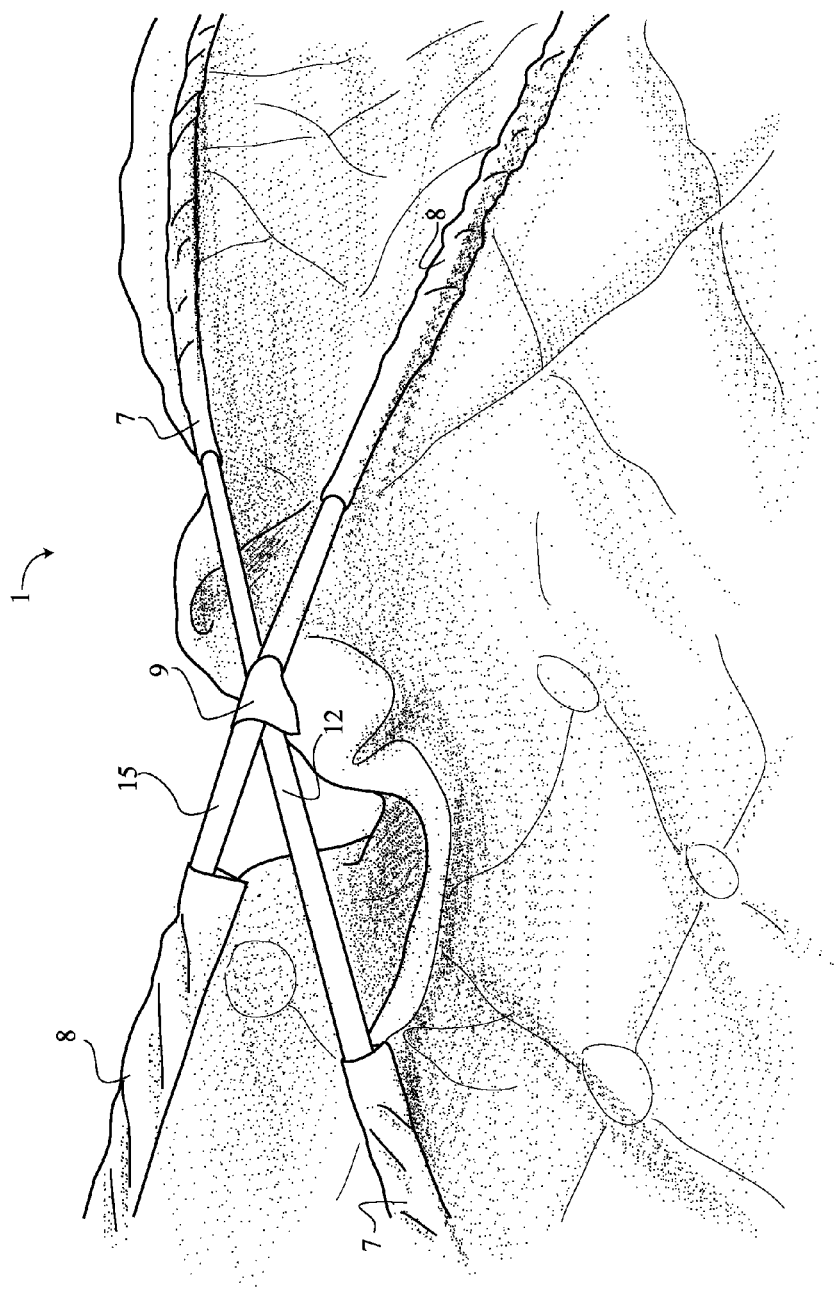
FIG. 2 is a right elevated view of the flexible poles of the present invention.

The first flexible pole 12 and the second flexible pole 15 each comprise two ends. There is a first end 13 of the first flexible pole 12 and a second end 14 of the first flexible pole 12, depicted in FIG. 3, FIG. 4, and FIG. 5. There is also a first end 16 of the second flexible pole 15 and a second end 17 of the second flexible pole 15. The flexible poles are attached to the collapsible canopy 1 by being inserted into either the first set of elongated sleeves 7 or the second set of elongated sleeves 8. The first flexible pole 12 traverses through the first set of elongated sleeves 7, such that its first end 13 is proximal to the first corner 3 of the elastic canopy perimeter 2 and its second end 14 is proximal to the third corner 5 of the elastic canopy perimeter 2. The second flexible pole 15 traverses through the second set of elongated sleeves 8, such that its first end 16 is proximal to the second corner 4 of the elastic canopy perimeter 2 and its second end 17 is proximal to the fourth corner 6 of the elastic canopy perimeter 2. The first flexible pole 12 and the second flexible pole 15 thus cross each other at the center of the collapsible canopy 1, where they pass through the central sleeve 9, illustrated in FIG. 2. While the flexible poles cross each other at the central sleeve, they are not directly connected to each other or the collapsible canopy 1. The flexible poles are simply held in position by the sleeves on the collapsible canopy 1.

In the preferred embodiment the first flexible pole 12 and second flexible pole 15 are made from fiberglass. In other embodiments, the flexible poles can be made of different materials (e.g. thermostat plastic) or covered with heat-shrink tubing, as long as the material is flexible. Additionally, the flexible poles could be segmented into smaller connected rods rather than being large single piece poles.

Figure 6:
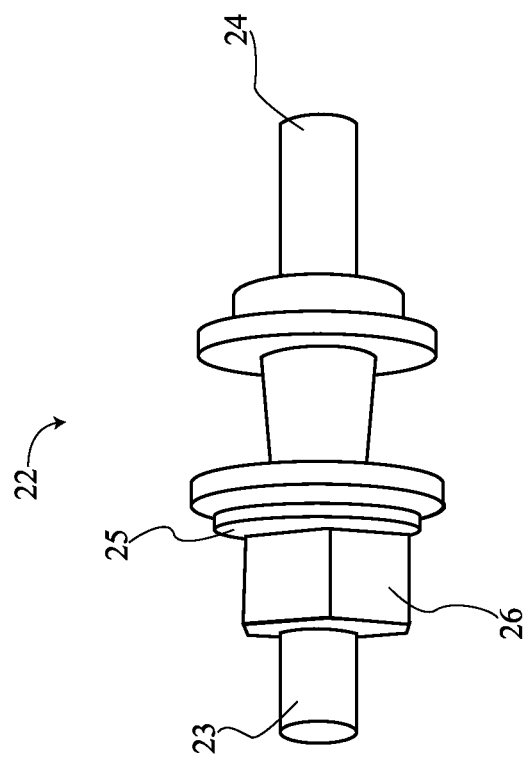
FIG. 6 is a side perspective view of the steam connector of the present invention.
Figure 7:
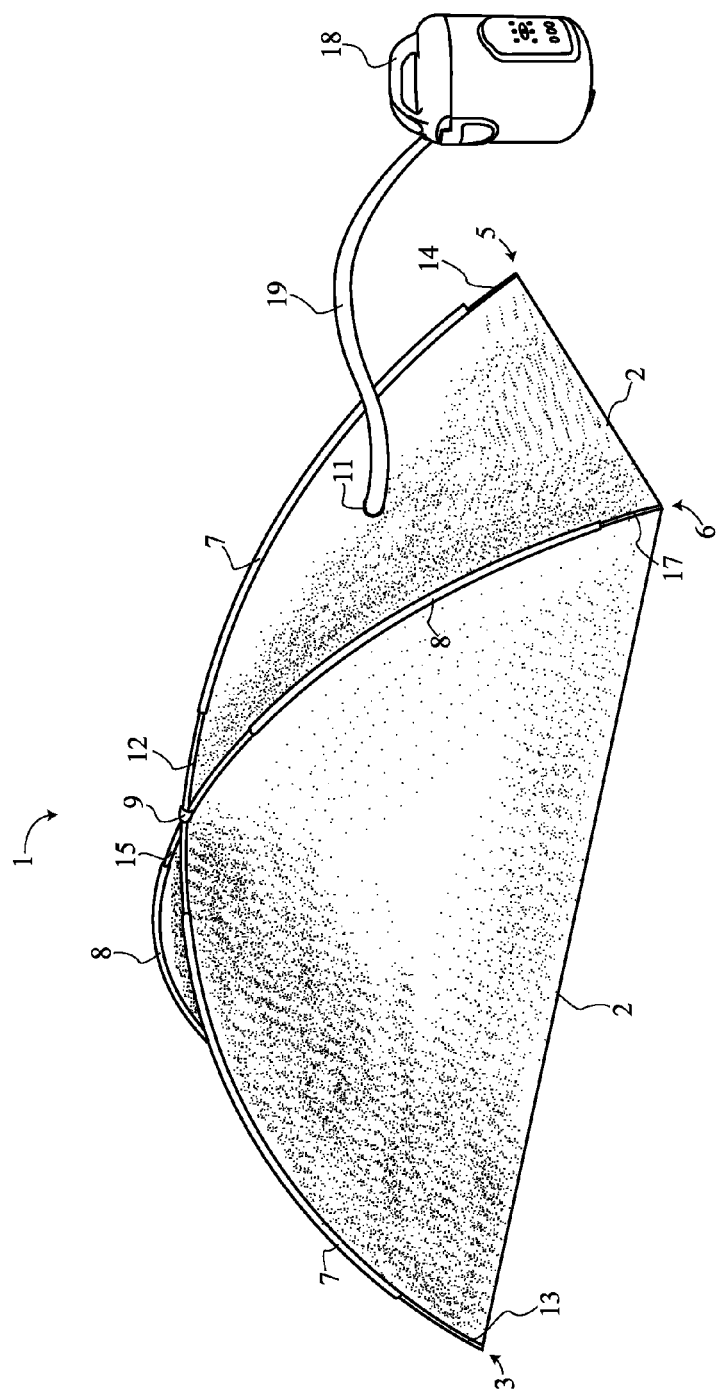
FIG. 7 is rear-right perspective view of the present invention.

A steam hose 19 is attached to a steam generator 18, separate from the collapsible canopy 1. The steam hose 19 is also attached to the steam connector 22 (shown in FIG. 6), which itself is inserted through the steam opening 11 of the collapsible canopy 1. In effect, the steam generator 18 is linked to the collapsible canopy 1 by the steam hose 19 and the steam connector 22, as illustrated in FIG. 7.

The steam hose 19 comprises a canopy end 20 and a generator end 21. The canopy end 20 is attached to the steam connector 22 while the generator end 21 attaches to the steam generator 18. The steam connector 22 comprises an interior end 23, an exterior end 24, a washer 25, and a nut 26. The interior end 23 of the steam connector 22 is inserted into the steam opening 11 of the collapsible canopy 1, leaving the exterior end 24 sticking out of the collapsible canopy 1. The washer 25 slides onto the interior end 23 and is secured to the steam connector 22, flush with the collapsible canopy 1, by screwing a nut 26 on the interior end 23. The interior end 23 includes threading to receive the nut 26. The canopy end 20 of the steam hose 19 attaches to the exterior end 24 of the steam connector 22.

In the preferred embodiment the generator is external to the collapsible canopy 1 and linked to the collapsible canopy 1 by the steam hose 19 and steam connector 22. In other embodiments multiple steam generators 18, steam hoses 19, and steam connectors 22 could be used to provide a greater amount of steam. This could be necessary if the collapsible canopy 1 has a large volume that needs to be filled with steam (perhaps a collapsible canopy 1 intended for multiple users), while a single steam generator 18 will likely be sufficient for smaller collapsible canopies 1 (such as for one person). Alternatively, the steam generator 18 could be directly connected to the collapsible canopy 1, being placed adjacent to the steam opening 11 and foregoing the use of a steam connector 22 and steam hose 19. The steam generator 18 would instead dispense steam directly through the steam opening 11 into the collapsible canopy 1. Potentially, the steam generator 18 could dispense steam into the collapsible canopy 1 from any opening or even below the collapsible canopy 1.

The base sheet 27 of the portable steam sauna helps to stabilize the collapsible canopy 1 on a flat surface, as well as protect said surface from water damage. As seen in FIG. 1, the base sheet 27 comprises an elastic base perimeter 28, a base cord 29, and a plurality of base attachments 30. The plurality of base attachments 30 further comprise a first base attachment 301, a second base attachment 302, a third base attachment 303, and a fourth base attachment 304. The base sheet 27, like the collapsible canopy 1, has a rectangular shape forming an open bottom. The elastic canopy perimeter 2 is adjacent to the open bottom. The first base attachment 301, second base attachment 302, third base attachment 303, and fourth base attachment 304 are consecutively positioned around the elastic base perimeter 28, with one attachment being located at each corner of the elastic base perimeter 28.

In the preferred embodiment, the plurality of base attachments 30 are pockets which receive the ends of the first flexible pole 12 and second flexible pole 15 through an open aperture, shown in FIG. 3. Potentially the plurality of base attachments 30 could be hook-and-loop fasteners, grommets, snap-fits, or laces. Depending on what method is used, the first flexible pole 12 and second flexible pole 15 may have to have matching attachment points. For example, if hook-and-loop fasteners are used for the base attachments 30, the attachment points on the flexible poles would need to include hook-and-loop fasteners to interface with the hook-and-loop fasteners on the base attachments 30.

The base cord 29 is integrated into the elastic base perimeter 28 (shown in FIG. 2) and can be used to tighten or loosen the elastic base perimeter 28, functioning similar to the canopy cord 201. The canopy cord 201 can be adjusted by hand, and secured through the use of a cord lock or other similar device. The combination of the elastic base perimeter 28 and the base cord 29 allows the base sheet 27 to be affixed to a flat surface, such as a table, upon which a person can rest during use of the steam sauna. The elastic base perimeter 28 fits around the flat surface while the base cord 29 can by tightened to further secure the base sheet 27 to the flat surface, similar to how the elastic canopy perimeter 2 is fitted to the base sheet 27.

Figure 11:
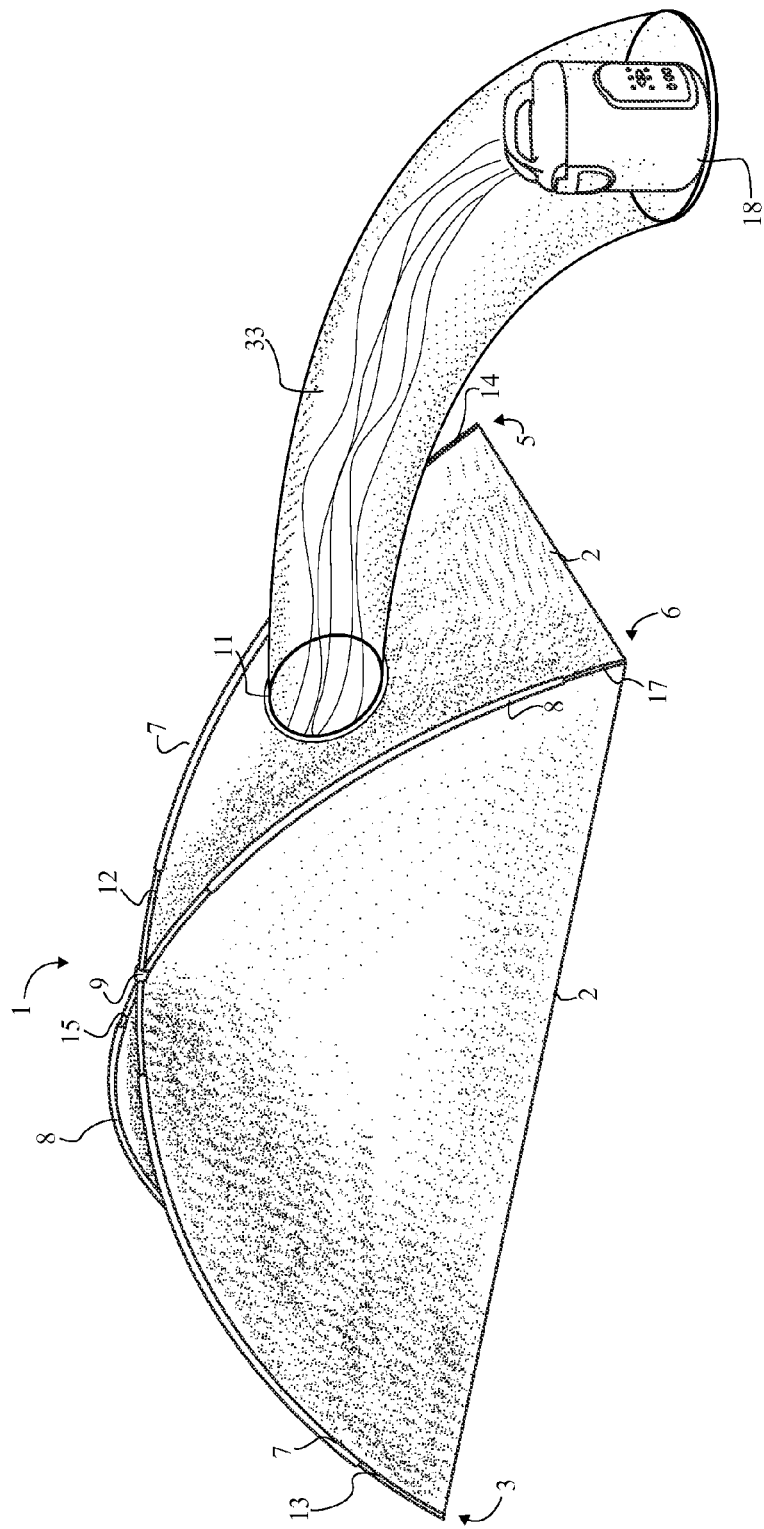
FIG. 11 is a rear-right perspective view of another embodiment of the present invention.

In a second embodiment slight variations can be made to the portable steam sauna to provide an alternate avenue of steam generation. Instead of using a steam connector 22 to secure the steam hose 19 to the collapsible canopy 1, a sleeve 33 could be integrated into the collapsible canopy 1, as illustrated in FIG. 11. This sleeve 33 would be an extension of the collapsible canopy 1 and function similar to the steam hose 19 in the preferred embodiment, routing steam from the steam generator 18 through a pathway into the collapsible canopy 1. The sleeve 33 is made of the same material as the collapsible canopy 1, being sewn onto the collapsible canopy 1. Unlike the preferred embodiment, a steam connector 22 is not needed since the sleeve 33 is directly connected (sewn) to the collapsible canopy 1 at the steam opening 11.

In a third embodiment the steam opening 11, steam connector 22, steam hose 19, and steam generator 18 are all replaced by a plurality of infrared heating elements 31. The plurality of infrared heating elements 31 emit heat in the infrared spectrum, directly warming a user of the present invention, rather than indirectly heating a user by heating the surrounding air. The plurality of infrared heating elements 31 are preferably either ceramic or carbon fiber. The plurality of infrared heating elements 31 can be made in a variety of sizes and are easily attached to the collapsible canopy 1. The plurality of infrared heating elements 31 should be evenly spaced inside the collapsible canopy 1, so that they uniformly heat the user. If the plurality of infrared heating elements 31 are not properly spaced then a user's body will become unevenly heated, with some body parts being too hot and others being not hot enough. The plurality of infrared heating elements 31 can be powered by a self-contained power source or be connected to an external power source, such as a wall socket or portable battery. The plurality of infrared heating elements 31 are attached to a plurality of mounting points 32 located on the interior of the collapsible canopy 1.

Figure 12:
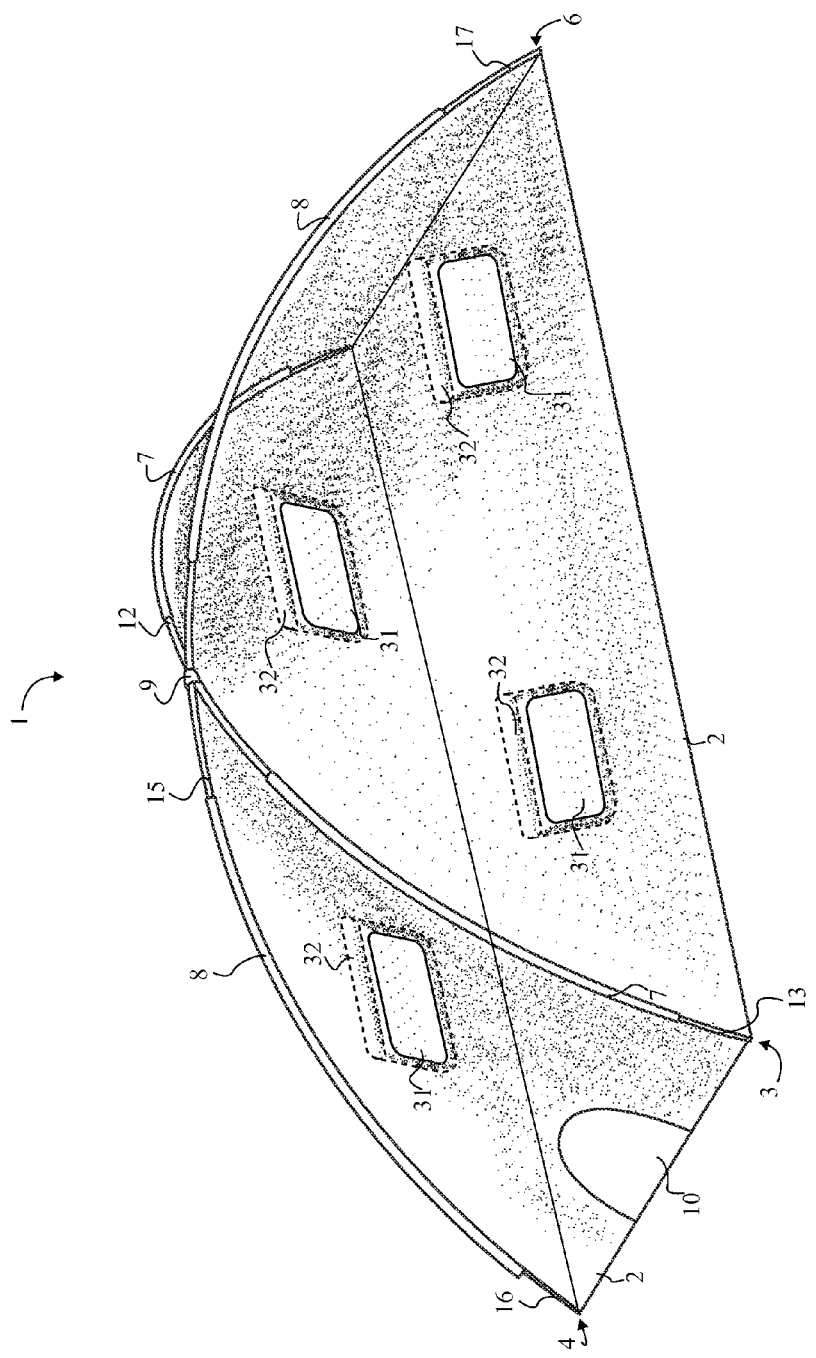
FIG. 12 is a front-right perspective view of another embodiment of the present invention.

As can be seen in FIG. 12, the plurality of infrared heating elements 31 are preferably secured to the collapsible canopy 1 by being inserted into pockets sewn into the interior of the collapsible canopy 1. Since the pockets, like the canopy, are made from a flexible material, they will not interfere with the collapsible nature of the present invention. In other embodiments the plurality of infrared heating elements 31 can be attached to the interior of the collapsible canopy 1 by other means. For example, hook-and-loop fasteners could be connected to the interior of the collapsible canopy 1 and the plurality of infrared heating elements 31. Alternatively, snap button fasteners, hooks, or any number of simple fasteners could be used to secure the plurality of infrared heating elements 31 to the interior of the collapsible canopy 1. As long as the fastener used is capable of supporting the plurality of infrared heaters and does not interfere with the collapsible nature of the present invention, a variety of options can be employed.

Instead of or in addition to a self-contained power source, the plurality of infrared heating elements 31 may be powered using electrical cords that plug into outside power sources, such as wall sockets. The collapsible canopy 1 includes small openings on the outside layer of the pockets, which allow the electrical cords to connect to the plurality of infrared heating elements 31. However, in this case care must be taken so that the openings are properly sealed against the electrical cords; improper sealing would allow outside air into the collapsible canopy 1 and diminish the effectiveness of the present invention. In other embodiments, an independent internal power source could be included with the collapsible canopy. This could be accomplished by simply providing an extra pocket to hold an internal battery, which could directly power the plurality of infrared heating elements 31 by means of internal wiring.

Using the plurality of infrared heating elements 31 can be advantageous over the embodiment employing a steam generator 18 and steam hose 19, as there are less issues with condensation. When using a traditional steam generator 18, condensation can form on the inside of the canopy. With the plurality of infrared heating elements 31, only the user is heated, so condensation on the interior of the collapsible canopy 1 is essentially a non-issue.

Figure 8:
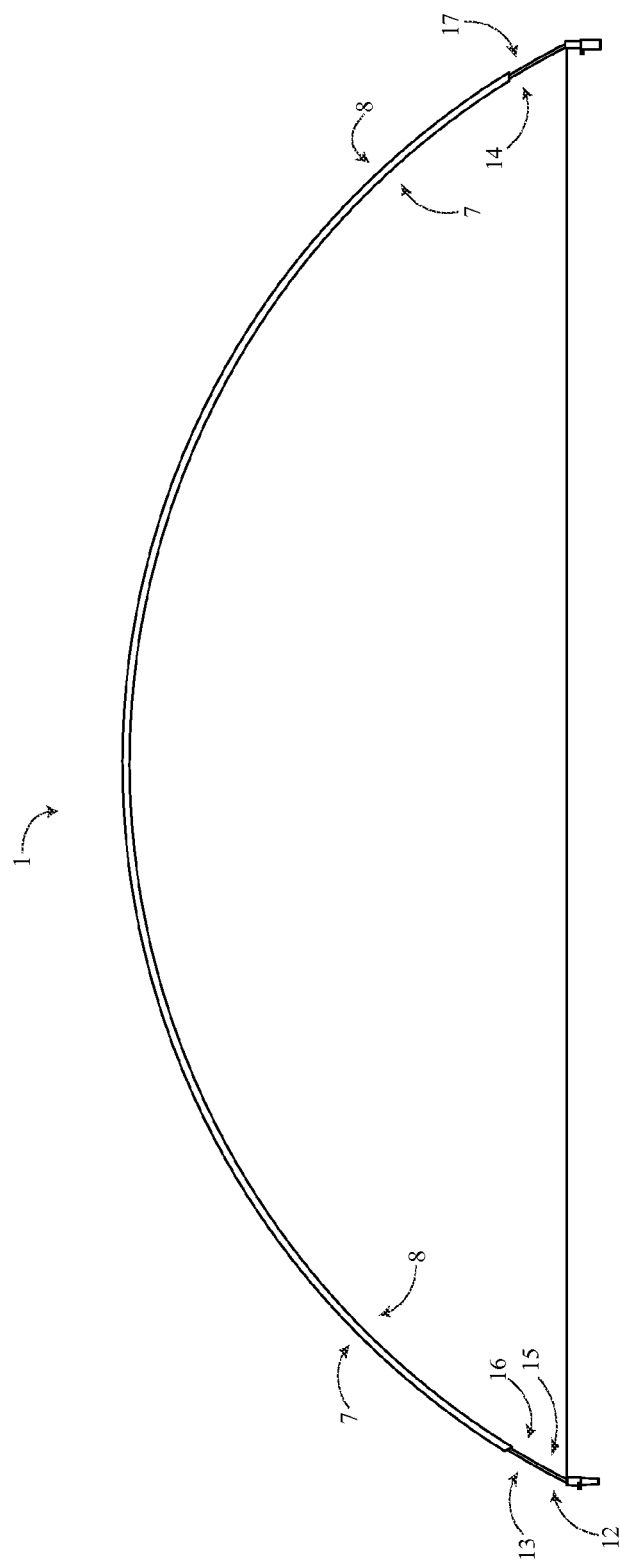
FIG. 8 is a drawing illustrating the collapsible canopy of the present invention showing the collapsible poles being brought together.
Figure 9:
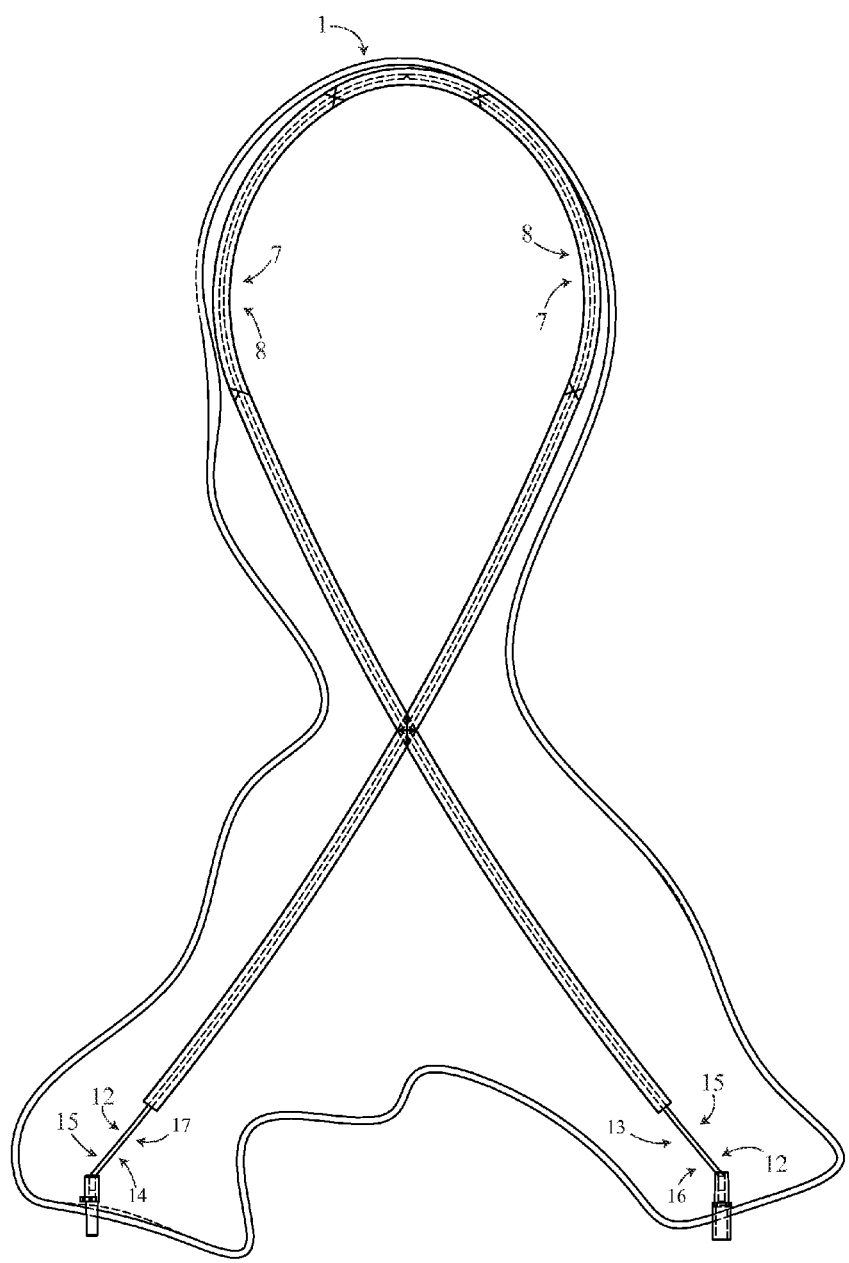
FIG. 9 is a drawing illustrating the collapsible canopy of the present invention being folded into a storage configuration.
Figure 10:
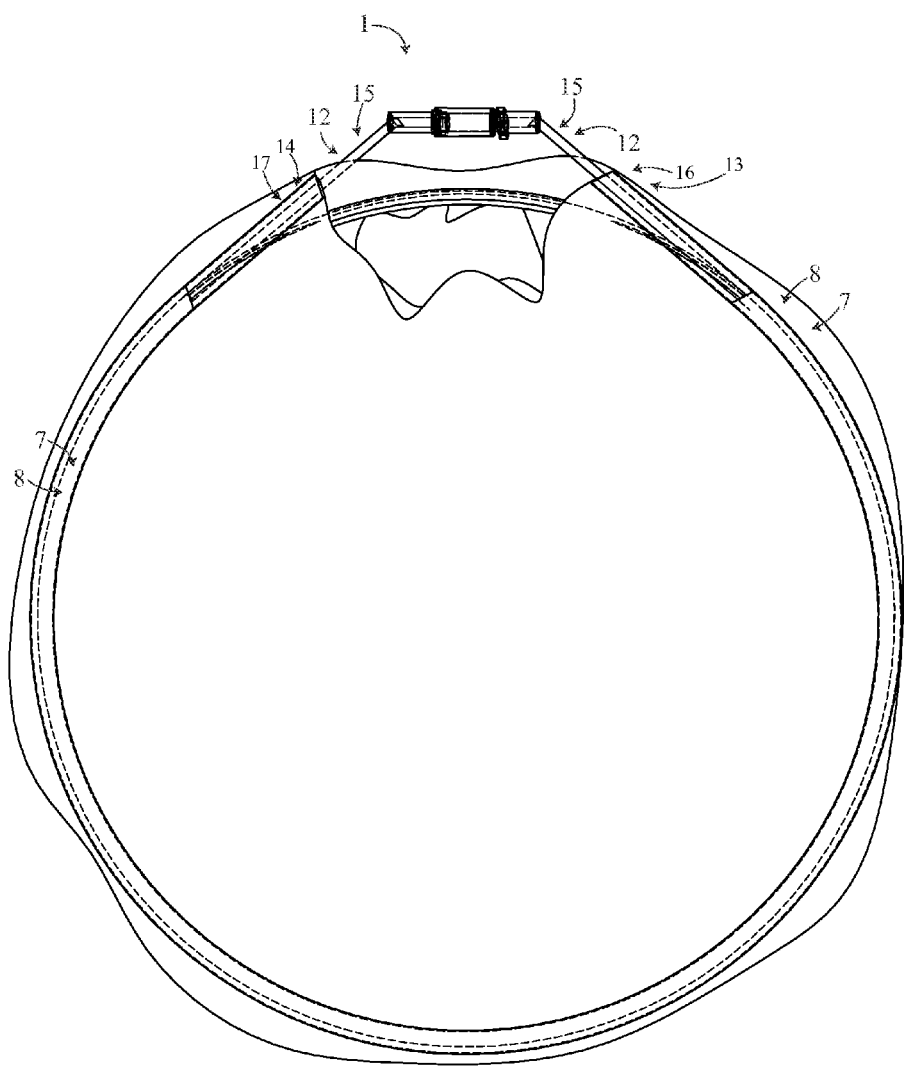
FIG. 10 is a drawing illustrating the collapsible canopy of the present invention in a storage configuration.

The collapsible canopy 1 can be switched between a use and a storage configuration. To be placed in a storage configuration, the flexible poles are brought together from a crossed position (where they would form the shape of an "X" from an overhead view), such that the flexible poles are parallel with each other (where they would form the shape of an "I" from an overhead view). This will result in the collapsible canopy 1 being flattened, illustrated in FIG. 8, with the flexible poles and collapsible canopy 1 sharing a plane. The flexible poles are then bent into the shape of a circle, (illustrated in FIG. 9 and FIG. 10) resulting in the collapsible canopy 1 taking the shape of a disc. To maintain this disc shape one of the flexible poles can folded over the other flexible pole, thus entwining the flexible poles and securing the collapsible canopy 1 in the storage configuration. The collapsible canopy 1 can then be stored in a carrying bag for easy transport. Potentially, a securing device, such as hook-and-loop belts, could be included to further secure the collapsible canopy 1 in the storage configuration. To return the collapsible canopy 1 to a use configuration, the securing device is released and the flexible poles are unfolded. The flexible poles may then be straightened and rotated, such that they form the shape of an "X" from an overhead view.

Setting up the portable steam sauna requires a flat surface, such as a massage table. Before setting up the portable steam sauna, the collapsible canopy 1 must be in the use configuration and the steam connector 22 must be secured to the collapsible canopy 1. If the collapsible canopy 1 is in the storage configuration, it must be returned to the use configuration, following the instructions presented earlier. Once the collapsible canopy 1 is in the use configuration, the steam connector 22 can be attached to the collapsible canopy 1. To do this, the steam connector 22 is inserted into the steam opening 11, with the interior end 23 being inside the collapsible canopy 1, and the exterior end 24 being positioned outside the collapsible canopy 1. The washer 25 is then placed over the interior end 23 of the steam connector 22, sliding over the interior end 23 until the washer 25 is flush with the collapsible canopy 1. The nut 26 is then screwed onto the interior end 23 of the steam connector 22, holding the washer 25 flush with the collapsible canopy 1. The base sheet 27 is then placed over the massage table, stretching the elastic canopy perimeter 2 over the massage table so that the elastic base perimeter 28 grips the massage table. The base cord 29 can then be tightened, firmly securing the base sheet 27 to the elastic base perimeter 28. Once the base perimeter has been set up, a user will lie down on the base sheet 27. Once the user is comfortable, the collapsible canopy 1 can be secured to the base perimeter. This is accomplished by attaching the flexible poles to the plurality of base attachments 30 and fitting the elastic canopy perimeter 2 over the base sheet 27. Before fitting the elastic canopy perimeter 2 to the base sheet 27, the collapsible canopy 1 should be oriented so that the head opening 10 is aligned with a user's neck, allowing the user's head to stick out of the collapsible canopy 1.

The first end 13 of the first flexible pole 12 is attached to the first base attachment 301, while the second end 14 of the first flexible pole 12 is attached to the third base attachment 303. Similarly, the first end 16 of the second flexible pole 15 is attached to the second base attachment 302, while the second end 17 of the second flexible pole 15 is attached to the fourth base attachment 304.

The elastic canopy perimeter 2 is stretched over the edges of the base sheet 27, after which the canopy cord 201 is pulled to tighten the elastic canopy perimeter 2. This helps to create a secure fit between the elastic canopy perimeter 2 and the base sheet 27. In this manner, the collapsible canopy 1 forms an enclosed area between the flat surface and collapsible canopy 1; the only exposed areas are the steam opening 11 and head opening 10 of the collapsible canopy 1.

After the base sheet 27 and collapsible canopy 1 have been deployed, the steam hose 19 and steam generator 18 can be connected to the collapsible canopy 1. The canopy end 20 of the steam hose 19 is fitted over the exterior end 24 of the steam connector 22, while the generator end 21 interfaces with the steam generator 18. With everything connected, the steam generator 18 can be activated to supply steam to the steam canopy by means of the steam hose 19.

Though the present invention has been described as being used with a massage table, it can be used in different configurations. For example, the present invention could be used inside a home, with the base sheet 27 securing to a yoga mat or other available surface, instead of being secured to a massage table. Potentially, the present invention could even be used in a vertical orientation, with the user standing up instead of lying down on a flat surface. In general, the collapsible and foldable nature of the collapsible canopy 1 allow the present invention to be easily used in and transported between a wide variety of environments.

Although the invention has been explained in relation to its preferred embodiment, it is to be understood that many other possible modifications and variations can be made without departing from the spirit and scope of the invention as hereinafter claimed.

What is claimed is:

1. A portable steam sauna comprises,
    a collapsible canopy;
    the collapsible canopy comprises an elastic canopy perimeter, a first corner, a second corner, a third corner, a fourth corner, a first set of elongated sleeves, a second set of elongated sleeves, a central sleeve, a head opening, and a steam opening;
    a first flexible pole and a second flexible pole;
    the first flexible pole and the second flexible pole each comprise a first end and a second end;
    a steam generator;
    a steam hose;
    a steam connector;
    a base sheet;
    the first corner, the second corner, the third corner, and the fourth corner being consecutively positioned along the elastic canopy perimeter;
    the third corner being positioned opposite the first corner;
    the fourth corner being positioned opposite the second corner;
    the first set of elongated sleeves and the second set of elongated sleeves being connected to the collapsible canopy;
    the central sleeve being connected to the collapsible canopy;
    the central sleeve being equidistant from the first corner, the second corner, the third corner, and the fourth corner;
    the base sheet comprises an elastic base perimeter, a base cord, and a plurality of base attachments;
    the plurality of base attachments comprises a first base attachment, a second base attachment, a third base attachment, and a fourth base attachment;
    the first base attachment, the second base attachment, the third base attachment, and the fourth base attachment being consecutively positioned along the elastic base perimeter;
    wherein the elastic base perimeter is fitted to a flat base surface;
    wherein the base cord is tightened to secure the base sheet to the flat base surface;
    the elastic canopy perimeter being attached to the elastic base perimeter;
    the collapsible canopy being attached to the base sheet;
    the first end of the first flexible pole being attached to the first base attachment;
    the second end of the first flexible pole being attached to the third base attachment;
    the first end of the second flexible pole being attached to the second base attachment; and
    the second end of the second flexible pole being attached to the fourth base attachment.

2. The portable steam sauna as claimed in claim 1 comprises,
    the head opening being positioned adjacent to the elastic canopy perimeter between the first corner and the second corner;
    the steam opening being positioned on the collapsible canopy; and
    the steam connector being attached to the steam opening.

3. The portable steam sauna as claimed in claim 1 comprises,
    the first set of elongated sleeves being linearly positioned between the first corner and the third corner;
    the second set of elongated sleeves being linearly positioned between the second corner and the fourth corner;
    the first flexible pole traversing through the first set of elongated sleeves;
    the first flexible pole traversing through the central sleeve;
    the second flexible pole traversing through the second set of elongated sleeves; and
    the second flexible pole traversing through the central sleeve.

4. The portable steam sauna as claimed in claim 1 comprises,
    the elastic canopy perimeter comprises a canopy cord;
    the elastic canopy perimeter being fitted over the base sheet; and
    wherein the canopy cord is tightened to secure the collapsible canopy to the base sheet.

5. The portable steam sauna as claimed in claim 1 comprises,
the steam connector being hollow;
the steam connector comprises an interior end, an exterior end, a washer, and a nut;
the steam connector being attached to the collapsible canopy;
the interior end traversing through the steam opening into the collapsible canopy;
the washer concentrically engaging with the interior end; and
the nut screwing onto the interior end.

6. The portable steam sauna as claimed in claim 5 comprises
the steam hose comprises a canopy end and a generator end;
the steam hose being attached to the steam connector;
the canopy end of the steam hose enveloping the exterior end of the steam connector; and
the generator end of the steam hose being attached to the steam generator.

7. A portable steam sauna comprises,
a collapsible canopy;
the collapsible canopy comprises an elastic canopy perimeter, a first corner, a second corner, a third corner, a fourth corner, a first set of elongated sleeves, a second set of elongated sleeves, a central sleeve, a head opening, and a steam opening;
a first flexible pole and a second flexible pole;
the first flexible pole and the second flexible pole each comprise a first end and a second end;
a steam generator;
a steam hose;
a steam connector;
a base sheet;
the base sheet comprises an elastic base perimeter, a base cord, and a plurality of base attachments;
the first corner, the second corner, the third corner, and the fourth corner being consecutively positioned along the elastic canopy perimeter;
the third corner being positioned opposite the first corner;
the fourth corner being positioned opposite the second corner;
the first set of elongated sleeves and the second set of elongated sleeves being connected to the collapsible canopy;
the first set of elongated sleeves being linearly positioned between the first corner and the third corner;
the second set of elongated sleeves being linearly positioned between the second corner and the fourth corner;
the first flexible pole traversing through the first set of elongated sleeves;
the second flexible pole traversing through the second set of elongated sleeves;
the central sleeve being connected to the collapsible canopy;
the central sleeve being equidistant from the first corner, the second corner, the third corner, and the fourth corner;
the plurality of base attachments comprises a first base attachment, a second base attachment, a third base attachment, and a fourth base attachment;
the first base attachment, the second base attachment, the third base attachment, and the fourth base attachment being consecutively positioned along the elastic base perimeter;
the elastic canopy perimeter comprises a canopy cord;
the elastic canopy perimeter being attached to the elastic base perimeter;
the collapsible canopy being attached to the base sheet;
the first end of the first flexible pole being attached to the first base attachment;
the second end of the first flexible pole being attached to the third base attachment;
the first end of the second flexible pole being attached to the second base attachment;
the second end of the second flexible pole being attached to the fourth base attachment;
wherein the elastic base perimeter is fitted to a flat base surface;
wherein the base cord is tightened to secure the base sheet to the flat base surface;
the elastic canopy perimeter being fitted over the base sheet;
wherein the canopy cord is tightened to secure the collapsible canopy to the base sheet;
the steam connector being hollow;
the steam connector comprises an interior end, an exterior end, a washer, and a nut;
the steam connector being attached to the collapsible canopy;
the interior end traversing through the steam opening into the collapsible canopy;
the washer concentrically engaging with the interior end; and
the nut screwing onto the interior end.

8. The portable steam sauna as claimed in claim 7 comprises,
the head opening being positioned adjacent to the elastic canopy perimeter between the first corner and the second corner;
the steam opening being positioned on the collapsible canopy; and
the steam connector being attached to the steam opening.

9. The portable steam sauna as claimed in claim 7 comprises,
the first flexible pole traversing through the central sleeve; and
the second flexible pole traversing through the central sleeve.

10. The portable steam sauna as claimed in claim 7 comprises
the steam hose comprises a canopy end and a generator end;
the steam hose being attached to the steam connector;
the canopy end of the steam hose enveloping the exterior end of the steam connector; and
the generator end of the steam hose being attached to the steam generator.

* * * * *